US012635899B2

(12) United States Patent
Wildhagen et al.

(10) Patent No.: US 12,635,899 B2
(45) Date of Patent: May 26, 2026

(54) METHOD FOR DETERMINING A POSITION OF A CATHETER TIP OF A CATHETER

(71) Applicant: B. Braun Melsungen AG, Melsungen (DE)

(72) Inventors: Jens Wildhagen, Hannover (DE); David Thalmann, Kaufungen (DE); Dejana Vukovic, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 150 days.

(21) Appl. No.: 18/277,166

(22) PCT Filed: Feb. 21, 2022

(86) PCT No.: PCT/EP2022/054217
§ 371 (c)(1),
(2) Date: Aug. 14, 2023

(87) PCT Pub. No.: WO2022/179974
PCT Pub. Date: Sep. 1, 2022

(65) Prior Publication Data
US 2024/0115154 A1 Apr. 11, 2024

(30) Foreign Application Priority Data
Feb. 23, 2021 (DE) ..................... 10 2021 201 702.9

(51) Int. Cl.
A61B 5/06 (2006.01)
A61B 5/00 (2006.01)
A61B 5/327 (2021.01)

(52) U.S. Cl.
CPC .............. *A61B 5/061* (2013.01); *A61B 5/327* (2021.01); *A61B 5/6852* (2013.01)

(58) Field of Classification Search
CPC ........ A61B 5/061; A61B 5/327; A61B 5/6852
See application file for complete search history.

(56) References Cited

U.S. PATENT DOCUMENTS

| | | | |
|---|---|---|---|
| 2009/0076483 A1* | 3/2009 | Danehorn | ............. A61B 34/20 604/528 |
| 2016/0066814 A1 | 3/2016 | Markowitz et al. | |
| 2019/0200886 A1* | 7/2019 | Welsh | .................... A61B 5/291 |
| 2020/0268953 A1 | 8/2020 | Ferrari et al. | |

FOREIGN PATENT DOCUMENTS

| | | | | |
|---|---|---|---|---|
| CN | 1531902 A | * | 9/2004 | |
| DE | 112012003687 | | 7/2014 | |
| WO | WO-2020052713 A2 | * | 3/2020 | ............. A61B 5/271 |

OTHER PUBLICATIONS

Machine translation of CN-1531902-A.*
Machine translation of WO-2020052713-A2.*
Schummer et al., "Modified ECG-guidance for optimal central venous catheter tip positioning. A transesophageal echocardiography controlled study," Randomized Controlled Trial, Anaesthesist, Oct. 2005; 54 (10), 9 pages.
Search Report received in International Application No. PCT/EP2022/054217 dated May 31, 2022, with translation, 6 pages.

* cited by examiner

*Primary Examiner* — Christopher Koharski

(74) *Attorney, Agent, or Firm* — CM Law; Christopher A. Rothe

(57) ABSTRACT

A method for determining a position of a catheter tip of a catheter, more particularly of a central venous catheter, in the body of a patient, a medical system equipped to carry out such a method, and the use of the method in catheterization.

8 Claims, 5 Drawing Sheets

METHOD FOR DETERMINING A POSITION OF A CATHETER TIP OF A CATHETER

CROSS-REFERENCE TO RELATED APPLICATION(S)

This application is the United States national phase entry of International Application No. PCT/EP2022/054217, filed Feb. 21, 2022, and claims priority to German Application No. 10 2021 201 702.9, filed Feb. 23, 2021. The contents of International Application No. PCT/EP2022/054217 and German Application No. 10 2021 201 702.9 are incorporated by reference herein in their entireties.

FIELD

The invention relates to a method for determining a position of a catheter tip of a catheter, in particular of a central venous catheter, in the body of a patient. The invention moreover relates to a medical system configured to carry out such a method.

BACKGROUND

Catheters, in particular central venous catheters, are generally known in medicine. When a catheter is applied, its catheter tip is introduced into a body-side access and advanced up to a desired location.

Central venous catheters are generally introduced via a vein of the upper body half into the venous system. The catheter tip is typically advanced into the area of the right atrium. A misdirected advance and/or insufficiently accurate positioning of the catheter tip can result in problems. To avoid such problems, it is necessary to check the position of the catheter tip at least after the application of the catheter. The position is best determined in real-time, i.e., already during the advancing movement. Different methods are known for this purpose in clinical practice.

In a known method, the position of the catheter tip is detected by x-ray after or even during the application. The radiation load accompanying this for the patient and involved medical personnel has health risks and opposes a broad application of the method. Moreover, the method requires complex apparatus and is relatively time-consuming and costly.

In a further known method, there is an electrocardiographic position check (for example W. Schumer et al.: "Optimierte Positionierung zentraler Venenkatheter durch eine modifizierte Anwendung der intravasalen Elektrokardiographie [optimized positioning of central venous catheter by a modified application of intravascular electrocardiography]". Anästhesist [anesthetist] 54 (2005), pages 983-990). In this case, an ECG (electrocardiograph) signal is derived between a skin electrode applied to the body surface of the patient and a Seldinger wire of the catheter. The known method makes use of the fact that the P wave of the ECG signal changes in dependence on the advance of the catheter tip. The P wave represents the electrical excitation of the atrium. A characteristic change of the P wave occurs as the catheter tip enters the atrium. The position check thus takes place via an observation of the derived ECG signal. The known electrocardiographic method only permits a confirmation of correct positioning in front of the right atrium. It is in particular not possible to determine the position of the catheter tip in areas remote from the atrium.

Moreover, a medical system is known under the trademark SHERLOCK 3CG™ Tip Confirmation System, which provides determining the position of the catheter tip by means of magnetic field sensors.

SUMMARY

The object of the invention to provide a method and a medical system of the type mentioned at the outset which offer advantages over the prior art.

The method according to the invention for determining a position of a catheter tip of a catheter, in particular a central venous catheter, in the body of the patient includes the following steps: a) detecting at least one first electrical voltage between a first electrode pair and detecting a second electrical voltage between a second electrode pair, wherein the first electrode pair are arranged spaced apart from one another along a first coordinate axis and the second electrode pair are arranged spaced apart from one another along a second coordinate axis on the body surface of the patient, and generating a first ECG signal and the second ECG signal, which represent a time curve of the respective electrical voltage and are assigned to the respective coordinate axis; b) detecting a first electrical reference voltage between a catheter electrode assigned to the catheter tip and a first reference electrode, preferably of the first electrode pair, detecting a second electrical reference voltage between the catheter electrode and a second reference electrode, preferably of the second electrode pair, and generating a first ECG reference signal and a second ECG reference signal, which represent the time curve of the respective electrical reference voltage; c) determining different transformed first ECG signals and different transformed second ECG signals for different transformation angles of the respective coordinate axis and by using the first ECG signal and the second ECG signal; d) determining a first transformation angle of the different transformation angles for which a deviation between the corresponding transformed first ECG signal and the first ECG reference signal is minimal, and a second transformation angle of the different transformation angles, for which a deviation between the corresponding transformed second ECG signal and the second ECG reference signal is minimal; e) determining the position of the catheter tip in relation to a coordinate system formed by the first coordinate axis and the second coordinate axis as a function of the determined first transformation angle and a position of the first reference electrode and of the determined second transformation angle and a position of the second reference electrode. The use of x-ray or electromagnetic radiation for determining the position of the catheter tip can be dispensed with by the solution according to the invention. In this way, on the one hand, the radiation load of the patient and the involved medical personnel is reduced. On the other hand, apparatus expenditure can be saved. This can be accompanied by a savings in time and costs. The invention proceeds in particular from the finding that the patient is often monitored by electrocardiography in any case during the application of the catheter, in other words is already connected to an ECG system. The solution according to the invention advantageously makes use of this circumstance in that—expressed in simplified terms—the position determination is carried out on the basis of different ECG signals and corresponding signal processing and evaluation of these ECG signals. The different ECG signals are derived, on the one hand, on the body surface and, on the other hand, in the interior of the body of the patient. The signal processing and/or evaluation comprises in particular a coordinate transformation of the derived ECG signals. The apparatus expenditure required for this purpose is comparatively minor. As a result, the solution according to the invention permits a noncomplex position determination "in real-time" while simultaneously avoiding health risks for the patient and the involved medical personnel.

Step a) provides detecting different electrical voltages between different electrode pairs attached to the patient's body surface. The detected electrical voltages result from the electrical activity of the cardiac muscle cells of the patient. Generating the ECG signals on the basis of the detected electrical voltages, i.e., potential differences between the individual electrodes of the electrode pairs, is carried out in a manner fundamentally known to a person skilled in the art. The different ECG signals are assigned to different coordinate axes. The different coordinate axes are preferably oriented orthogonally. However, this is not absolutely required. Furthermore, the different coordinate axes are preferably body axes of the patient. Expressed in simplified terms, step a) comprises deriving different surface ECG signals. It is to be understood that depending on the number of the electrodes and/or electrode pairs used, more than the first and second ECG signal can also be derived. For example, in particular a Goldberger, Einthofen, thoracic wall, or Nehb lead, which is known to a person skilled in the art, having electrodes arranged accordingly on the body surface can be performed.

Step b) provides detecting different reference voltages, namely at least the first and second reference voltage. The electrical reference voltages are each detected between the catheter electrode and a reference electrode. The catheter electrode is assigned to the catheter tip, preferably arranged and/or formed thereon. The reference electrodes are preferably each assigned to one of the electrode pairs. In contrast to the surface ECG signals detected/generated in step a), the ECG reference signals—in any case partially, namely by means of the catheter electrode—are derived in the body interior of the patient. If the catheter is, for example, a venous catheter, this can also be referred to as an endovascular lead. The catheter-side lead can be wired or wireless. For example, the catheter electrode can be formed by a distal front end of the Seldinger wire or another conductor wire. Alternatively, the catheter electrode can be formed by a distal front end opening of a catheter lumen filled—during the application of the catheter—with electrically conductive liquid, in particular body liquid. It is obvious that the catheter can include multiple catheter electrodes. In this case, not every catheter electrode must be assigned to the catheter tip. For example, multiple catheter electrodes can be formed and/or arranged spaced apart from one another along a longitudinal axis extending between a distal and a proximal end of the catheter. If multiple catheter electrodes are provided, in addition to the position of the catheter tip, a determination of the position of further sections of the catheter and/or the orientation of the catheter tip can take place.

Step c) provides a coordinate transformation of the ECG signals assigned to the different coordinate axes. The coordinate transformation of signals is known as such at least in the field of signal processing and evaluation. For example, the coordinate transformation can be data-based and/or computer-assisted. Standard algorithms are known for this purpose, as are used, among other things, for mixing complex signals. Expressed in simplified terms, in this context one of the two coordinate axes can be assumed as the real part and the other of the coordinate axes as the imaginary part. The coordinate transformation is preferably carried out in the form of a coordinate rotation in the time curve by multiplication with a fixed offset angle. The coordinate transformation is carried out for (many) different angles. As a result, different transformed ECG signals are provided for different transformation angles. The transformed ECG signals differ in particular with regard to their respective time curve and/or their signal form.

Step d) provides, in other words, a comparison of the ECG reference signals to the transformed ECG signals. By means of the comparison, those transformation angles are determined for which a deviation between the corresponding transformed ECG signals and the respective ECG reference signal is minimal. The determination of the different transformation angles, namely the first and second transformation angles, is preferably computer-assisted. Furthermore, an amplitude correction of the ECG signals to be evaluated preferably takes place. In this way, it is possible to prevent a possible amplitude error from corrupting the determination of the first and second transformation angles.

Step e) comprises the actual position determination on the basis of the determined first transformation angle and the determined second transformation angle. The position is determined here in relation to the first and second coordinate axes and relative to the position of the first and/or second reference electrode. Expressed in simplified terms, an intersection point between a first and a second straight line is preferably determined. The first straight line has its origin in the position of the first reference electrode and is inclined by the first transformation angle relative to the first coordinate axis. The second straight line has its origin in the position of the second reference electrode and is inclined by the second transformation angle relative to the second coordinate axis. In still other words, the position determination is carried out as a function of the first transformation angle, the second transformation angle, the positions of the first and second reference electrode, in relation to the coordinate system formed by the coordinate axes, and using simple geometrical relationships.

The solution according to the invention is particularly advantageously suitable for central venous catheters, PICCS (Peripherally Inserted Central Venous Catheter), and so-called midlines. The solution according to the invention is not restricted to such catheters, however, but is also advantageously suitable, for example, for pulmonary catheters, dialysis catheters, and/or arterial catheters.

In one embodiment of the invention, step c) is carried out using vector ECG data formed at least from the first ECG signal and the second ECG signal. A vector ECG, which can also be referred to as a vector cardiogram, is to be understood as a three-dimensional representation of a time curve of the electrical potential differences generated by the heart. In other words, the vector ECG data represent an absolute value and a direction of the electrical potential differences generated by the cardiac muscle activity over time. Reference is also often made in this context to a vector loop. The inventors have recognized that a position determination based on vector ECG data offers special advantages.

In a further embodiment of the invention, step d) comprises: comparing the signal forms of the different transformed respective ECG signals to the signal form of the respective ECG reference signal, wherein the respective deviation is determined on the basis of an error criterion and/or without consideration of differences in the respective signal amplitudes. The inventors have recognized that differences in the respective signal amplitudes of the ECG signals to be compared can result in an insufficiently accurate determination of the first and/or second transformation angle. This can ultimately result in an inaccurate determination of the position of the catheter tip. To counteract this, the deviations between the different transformed first ECG signals and the first ECG reference signal are determined by means of a comparison of the signal forms. The same applies, mutatis mutandis, with regard to the transformed second ECG signals and the second ECG reference signal. In particular an MSE criterion (mean square error) can be used as an error criterion. In a further embodiment, the deviation is determined with consideration of differences in the respective signal amplitudes.

In a further embodiment of the invention, at least one further electrical reference voltage is determined between the catheter electrode and a further reference electrode, preferably of the electrode pairs, and a further ECG reference signal is generated, which represents the time curve of the further electrical reference voltage, wherein steps d) and e) are carried out in consideration of the further ECG reference signal. Further improved accuracy of the position determination can be achieved in this way. The further reference electrode can be assigned, for example, to the first electrode pair and thus the first coordinate axis. Alternatively, the further reference electrode can be assigned to the second electrode pair and thus the second coordinate axis. In this embodiment of the invention, step d) accordingly comprises the determination of a further transformation angle, for which a deviation in relation to the further ECG reference signal is minimal. The further transformation angle can be assigned to the first or second coordinate axis. Expressed visually, further intersection points between the above-mentioned first and second straight line and additionally a further straight line are determined for the position determination. The position can be determined approximately and/or on average as a function of the multiple intersection points. The further straight line has its origin in the position of the further reference electrode and is inclined by the further transformation angle relative to the first or second coordinate axis, depending on which of the two coordinate axes the further reference electrode is assigned to.

In a further embodiment of the invention, the position of the catheter tip is determined in relation to a three-dimensional coordinate system and as a function of a third transformation angle and a position of a third reference electrode, which are each assigned to a third coordinate axis. The solution according to the invention enables the position determination first in relation to the coordinate system formed by the first and second coordinate axis and thus in relation to a plane. This plane, if the coordinate system is assigned to the body axes of the patient, can be, for example, a frontal, transverse, or sagittal plane. In an expansion thereto, this embodiment of the invention enables a three-dimensional position determination. The third coordinate axis is preferably orthogonal to the first and/or second coordinate axis. In this embodiment of the invention, step a) preferably provides detecting a third electrical voltage and generating a third ECG signal. The third electrical voltage is preferably detected between a third electrode pair. The third electrode pair is preferably arranged spaced apart from one another along the third coordinate axis on the body surface of the patient. Accordingly, the third ECG signal is assigned to the third coordinate axis. Furthermore, step b) preferably provides detecting a third electrical reference voltage. This is detected between the catheter electrode and the third reference electrode, preferably of the third electrode pair. Furthermore, step b) preferably provides generating a third ECG reference signal on the basis of the detected third electrical reference voltage. With respect to step c), a determination of different transformed third ECG signals for different transformation angles of the third coordinate axes using the third ECG signal is preferably provided. The third transformation angle is determined in step d). These statements made with regard to the determination of the first and/or second transformation angle apply, mutatis mutandis, in this regard. The determination of the position in step e) comprises—visually speaking—a determination of an intersection point in space between the above-mentioned first and second straight lines and a third straight line. Its origin is located at the position of the third reference electrode. Moreover, the third straight line is inclined by the third transformation angle relative to the third coordinate axis.

In a further embodiment of the invention, multiple positions of the catheter tip are determined continuously in time during an advance movement of the catheter in the body, wherein a movement path of the catheter tip is determined as a function of the determined multiple positions. The movement path represents a chronological progression of the position of the catheter tip during the advance movement. Errors in the application of the catheter can be counteracted in a further improved manner by this embodiment of the invention. Further improved patient safety is achieved in this way.

In a further embodiment of the invention, the method includes the following steps: displaying the determined position and/or the movement path of the catheter tip. In this way, the position and/or the movement path can be supervised in a simple and reliable manner by medical personnel. The display is preferably carried out by means of a display unit configured for this purpose, for example by means of a display, a display screen, a projection device, or the like.

The invention moreover relates to a medical system for carrying out the method according to the preceding description, including a catheter, in particular a central venous catheter, having a catheter tip, to which at least one catheter electrode is assigned, at least three electrodes provided for arrangement on a body surface of a patient, which form a first electrode pair and a second electrode pair, and including an evaluation unit, which is connected to the catheter electrode and the electrodes and is configured to carry out the steps of the method according to the preceding description. The evaluation unit is preferably configured to carry out steps a) to e). The medical system according to the invention enables a position determination of the catheter tip which is noncomplex with regard to apparatus and thus saves time and costs. At the same time, a health impairment of the patient and the involved medical personnel due to x-ray and/or electromagnetic radiation typically used for position determination can be avoided. Otherwise, reference is made to the disclosure for the method according to the invention to avoid repetitions. These statements made there with regard to advantages accompanying the solution according to the invention apply mutatis mutandis to the medical system according to the invention.

In a further embodiment of the invention, the medical system includes a display unit, which is configured to display a position and/or movement path of the catheter tip determined by means of the evaluation unit. The display unit can in particular include a display, a display screen, a projection device, or the like.

Further advantages and features of the invention result from the following description of preferred exemplary embodiments of the invention, which are illustrated on the basis of the drawings.

DETAILED DESCRIPTION

Figure 1:
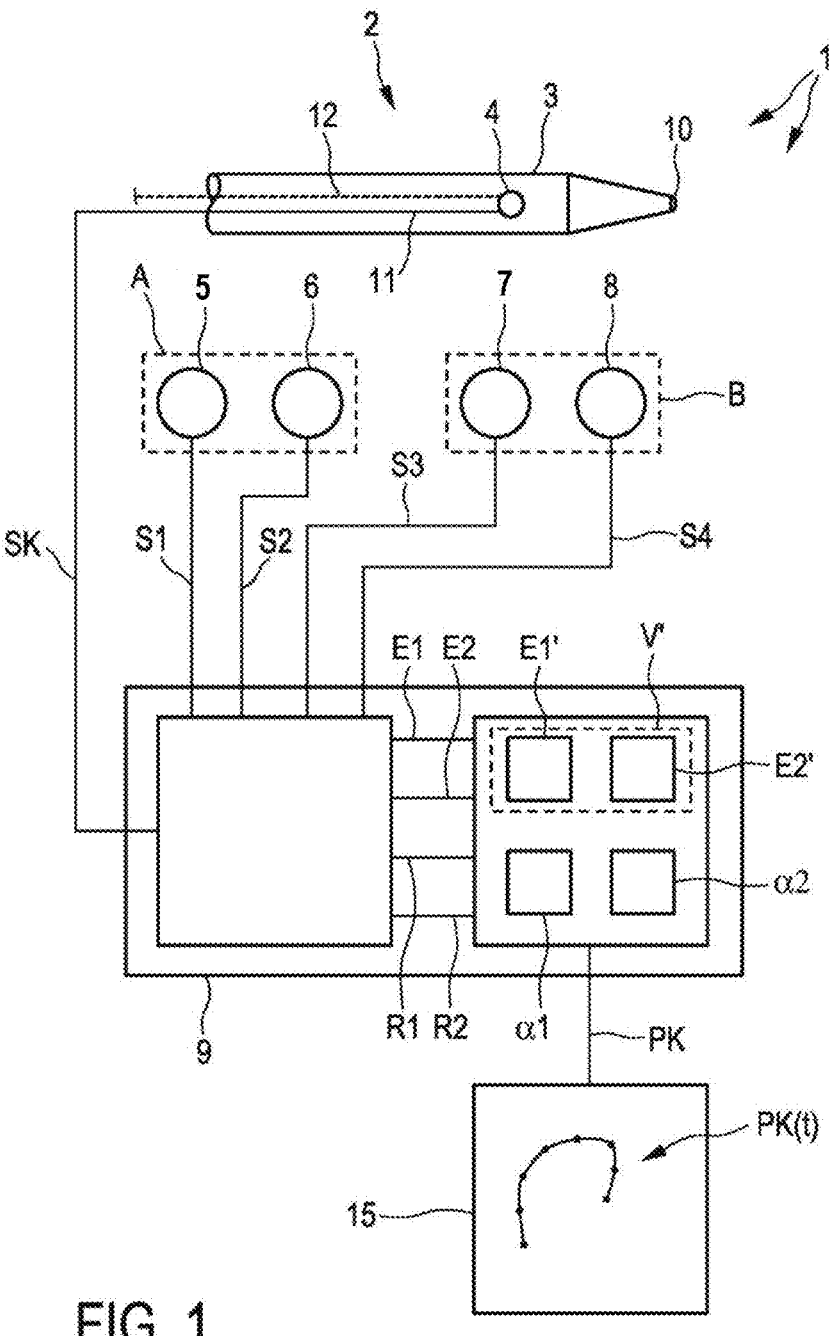
FIG. 1 shows a schematic view of an embodiment of a medical system according to the invention, which is configured to carry out an embodiment of the method according to the invention and includes a catheter, multiple electrodes, an evaluation unit, and a display unit.

According to FIG. 1, a medical system 1 is provided with a catheter 2, on the catheter tip 3 of which at least one catheter electrode 4 is arranged and/or formed, with at least three electrodes 5, 6, 7, 8, which are configured to be arranged on a body surface O of the patient M, and with an evaluation unit 9. The medical system 1 is shown schematically and very simplified on the basis of FIG. 1.

The catheter 2 is only shown in the area of its catheter tip 3. The catheter tip 3 is arranged at a distal end of the catheter 2. In the present case, the catheter 2 is a central venous catheter.

In embodiments which are not shown in the drawings, the catheter can instead be in particular a PICC catheter, a so-called midline, a pulmonary catheter, a dialysis catheter, or an arterial catheter.

In the illustrated embodiment, the catheter electrode 4 is arranged at a known distance, not designated in more detail, from a distal end 10 of the catheter 2 at the catheter tip 3.

The catheter electrode 4 is configured to detect an electrical potential SK prevailing at the catheter tip 3 and is connected in a wireless and/or wired manner to the evaluation unit 9 for the purpose of signal transmission. This detection and/or transmission can also be designated as a lead according to a speech usage typical in medicine.

Both a wireless and a wired lead are shown schematically in FIG. 1, wherein preferably either a wired or a wireless lead is provided.

For the wired lead, the catheter 2 includes a conductor wire 11. The conductor wire 11 establishes an electrically conductive connection between the catheter electrode 4 and the evaluation unit 9. The catheter electrode 4 can be manufactured as a separate component and/or section and can then be electrically conductively connected to the conductor wire 11. Alternatively, the catheter electrode 4 can be formed by a distal front end of the conductor wire 11. The conductor wire 11 can be a wire especially designed for the lead of the electrical potential SK or a Seldinger wire. The latter is used in a manner known to a person skilled in the art during an application of the catheter by means of the so-called Seldinger technique.

For the wireless lead, the catheter 2 can include a catheter lumen 12 assigned to the catheter electrode 4. In the application of the catheter 2, the catheter lumen 12 is provided in a manner known to a person skilled in the art for conducting liquid. For example, a medical liquid can be administered to or a body fluid can be taken from the patient M by means of the catheter lumen 12. In the present case, the catheter lumen 12 is additionally used for said lead, wherein this takes place during the application of the catheter 2 via said (electrically conductive) liquid located in the catheter lumen 12. The catheter lumen 12 is shown schematically and very simplified by dashed lines on the basis of FIG. 1. The catheter electrode 4 can be formed by a distal front end opening of the catheter lumen 12.

In the illustrated embodiment, the medical system 1 has a total of four electrodes 5, 6, 7, 8 which can also be referred to as first electrode 5, second electrode 6, third electrode 7, and fourth electrode 8. In embodiments which are not shown in the drawings, only three or more than the four electrodes shown in the present case are provided.

The electrodes 5, 6, 7, 8 are configured to be arranged on the body surface O of the patient M (FIG. 2) and—in contrast to the catheter electrode 4—can also be referred to as skin electrodes.

The first electrode 5 and the second electrode 6 form a first electrode pair A in the present case. The third electrode 7 and the fourth electrode 8 form a second electrode pair B. If more than the four electrodes shown in the present case are provided, more than only two electrode pairs can be provided or formed.

Moreover, it is to be understood that in principle three electrodes are sufficient to form the two electrode pairs shown in the present case, if at least one of the electrodes is assigned to both electrode pairs.

The electrodes 5, 6, 7, 8 are each configured for the derivation of an electrical potential S1 to S4 from the body surface O. The electrical potentials S1 to S4 can also be referred to as first electrical potential S1, second electrical potential S2, third electrical potential S3, and fourth electrical potential S4.

The electrodes 5 to 8 are each connected to the evaluation unit 9 for signal transmission and/or derivation. In the embodiment shown, wired connections (not designated in greater detail) are provided for this purpose between the electrodes 5 to 8 and the evaluation unit 9. This is to be understood solely as an example.

An application of the catheter 2 takes place in a manner fundamentally known to a person skilled in the art. The catheter 2 is typically introduced here via a vein of the upper body half of the patient M into the patient's venous system. The catheter tip 3 is advanced up into the area of the right atrium of the heart H. It is known that insufficiently accurate positioning of the catheter tip 3 is problematic. To avoid problems, a position determination already during the application of the catheter 2 is desirable, so that the position of the catheter tip 4 during its advance movement within the venous system can be supervised and tracked by medical personnel. The medical system 1 permits such a position determination. For more detailed explanation, reference is made hereinafter in particular to FIGS. 2 to 5.

Figure 2:
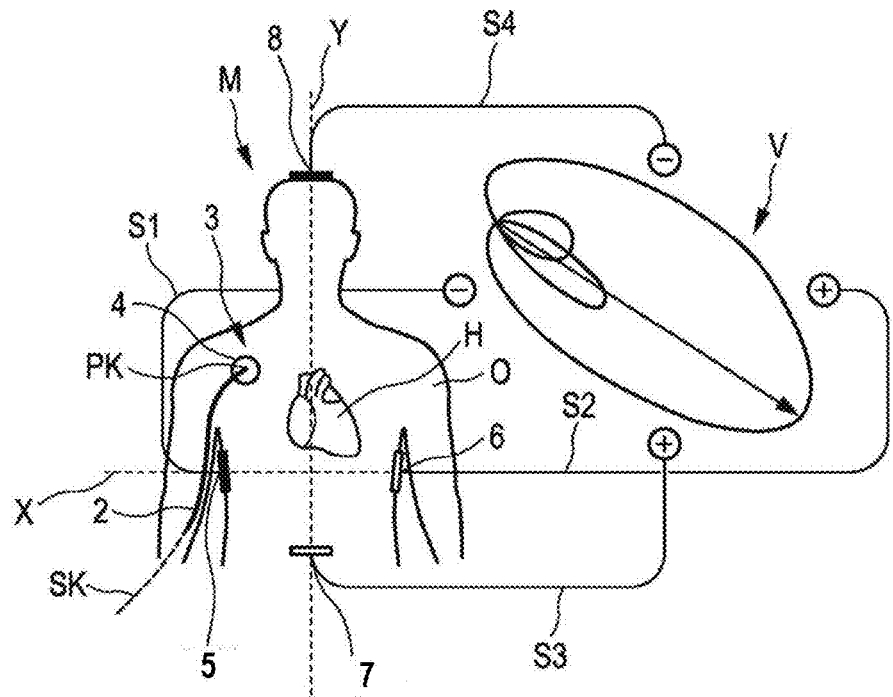
FIG. 2 shows a schematic view to illustrate a fundamental functionality of the medical system according to FIG. 1.
Figure 3:
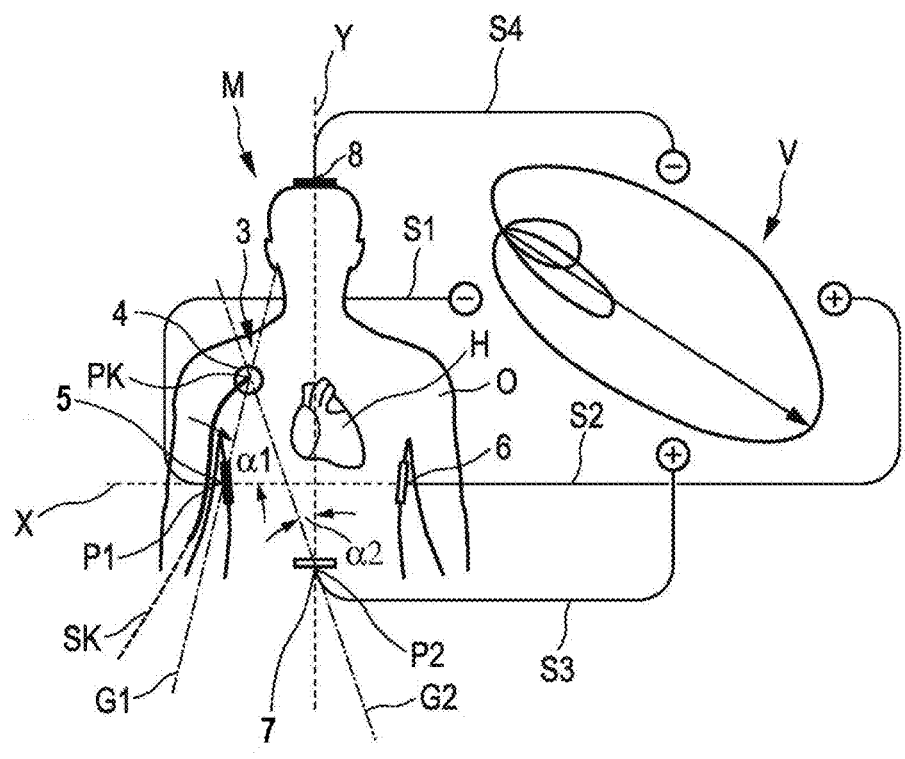
FIG. 3 shows a further schematic view to illustrate the fundamental functionality.

FIGS. 2 and 3 show, schematically and very simplified, an exemplary application situation of the medical system 1. In this application situation, the catheter 2 is introduced through a body-side access (not designated in more detail) in the area of the crook of the arm of the patient M into the venous system, wherein the catheter tip 3 occupies a position PK in the interior of the body of the patient M.

The first electrode 5 and the second electrode 6 are arranged spaced apart from one another along a first coordinate axis X on the body surface O. The third electrode 7 and the fourth electrode 8 are arranged spaced apart from one another along a second coordinate axis Y on the body surface O. The arrangement shown in FIGS. 2 and 3 is to be understood as schematic and very simplified and is used solely to illustrate the fundamental application and functionality of the medical system 1. In particular, the arrangement of the third electrode 8 on the crown of the patient M is used solely for improved illustration in the drawing.

The first coordinate axis X and the second coordinate axis Y are oriented orthogonally to one another and span a coordinate plane in the embodiment shown, which corresponds to the frontal plane of the patient M. The spanned coordinate plane can be different due to a correspondingly modified arrangement of the electrodes 5 to 8 and can correspond, for example, to a transverse or sagittal plane of the patient M.

Figure 5:
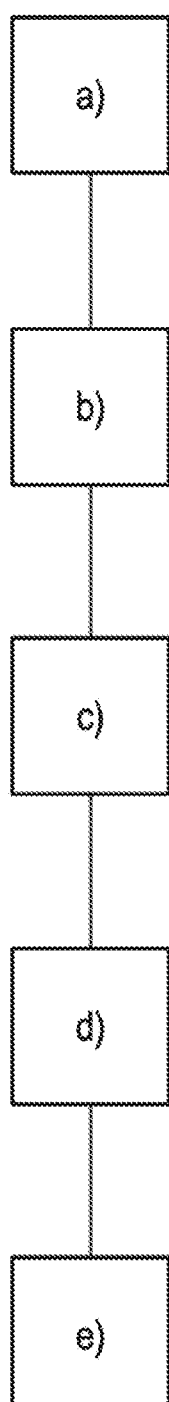
FIG. 5 shows individual steps of an embodiment of a method according to the invention in a schematic diagram representation.

Starting from the application situation shown, the actual position determination takes place by carrying out the method schematically illustrated on the basis of FIG. 5, which includes steps a) to e) in the present case:

Step a) provides that a first electrical voltage is detected between the first electrode pair A and a second electrical voltage is detected between the second electrode pair B. The electrical voltages correspond to a potential difference of the electrical potentials detected by means of the electrodes of the respective electrode pair. The first electrical voltage can insofar also be referred to as the potential difference S1-S2. The second electrical voltage can also be referred to as the potential difference S3-S4. In this context, it is to be noted that the assignment of the schematically shown positive and negative poles shown in FIGS. 2 and 3 is solely by way of example and can also be reversed, for example.

The electrical potentials S1 to S4 or electrical voltages are derived in the above-described manner. Actual signal processing and/or evaluation is carried out by means of the evaluation unit 9, wherein a first ECG signal E1 and a second ECG signal E2 are generated on the basis of the detected electrical potentials S1 to S4. The first ECG signal E1 represents a time curve of the electrical voltage between the first electrode 5 and the second electrode 6 of the first electrode pair A and is assigned to the first coordinate axis X. The second ECG signal E2 represents a time curve of the electrical voltage between the third electrode 7 and the fourth electrode 8 of the second electrode pair B and is assigned to the second coordinate axis Y.

The ECG signals E1, E2 are shown in FIGS. 2 and 3 in a manner fundamentally known to a person skilled in the art in the form of an exemplary vector loop. The vector loop represents vector ECG data V formed from the first ECG signal E1 and the second ECG signal E2.

Step b) comprises detecting a first electrical reference voltage between the catheter electrode 4 and a first reference electrode. Moreover, a second electrical reference voltage is detected between the catheter electrode 4 and a second reference electrode. In the present case, the first reference electrode is assigned to the first electrode pair A and is formed by its first electrode 5. Accordingly, the second reference electrode is assigned to the second electrode pair B and is formed by its third electrode 7. In an embodiment which is not shown in the drawings, the reference electrodes can be formed by electrodes separate from the electrode pairs.

The first reference voltage corresponds to an electrical potential difference between the electrical potential SK of the catheter electrode 4, which can also be referred to as the catheter potential, and the first electrical potential S1. The second electrical voltage corresponds to an electrical potential difference between the catheter potential SK and the third electrical potential S3. Starting from the two detected reference voltages, a first ECG reference signal R1 and a second ECG reference signal R2 are generated by means of the evaluation unit 9. The first ECG reference signal R1 represents the time curve of the first electrical reference voltage between the catheter electrode 4 and the first reference electrode 5. The second ECG reference signal R2 represents the time curve of the second electrical reference voltage between the catheter electrode 4 and the second reference electrode 7.

Step c) comprises determining different transformed first ECG signals E1' and different transformed second ECG signals E2' for different transformation angles of the respective coordinate axis X, Y using the first and the second ECG signal E1, E2. Expressed in simplified terms, this coordinate transformation is carried out by a rotation of a vector profile of the vector loop (FIGS. 2, 3). Such a coordinate transformation can be carried out by standard algorithms—in any case known in principle in the area of signal processing and evaluation. Such standard algorithms are known, for example, for the mixing of complex signals. For this purpose, visually speaking, the first ECG signal E1 assigned to the first coordinate axis X can be assumed as the real part. The second ECG signal E2 assigned to the second coordinate axis Y can be assumed as the imaginary part. Said coordinate transformation takes place in the time curve by multiplication with a preferably fixed offset angle. Such a coordinate transformation, more precisely: rotation of the underlying coordinate axis, is carried out for many different transformation angles. A large number of different transformed first ECG signals and second ECG signals is insofar determined, which are designated by only a single reference sign, namely E1' or E2', respectively, for simplified reference. As a result of the coordinate transformation, different signal curves of the underlying ECG signal are provided for different transformation angles.

Step d) comprises a determination of a first transformation angle α1 and a second transformation angle α2. The first transformation angle α1 is that transformation angle of the coordinate transformation carried out in step c) for which a deviation between the transformed first ECG signal E1' and the first ECG reference signal R1 is minimal. The second transformation angle α2 is that transformation angle of the coordinate transformation for which a deviation between the transformed second ECG signal E2' and the second ECG reference signal R2 is minimal. In other words, step d) comprises a comparison of the leads formed using the catheter electrode 4 and the reference electrodes 5, 7 with the transformed leads of the electrode pairs A, B. The goal of this comparison is to find those transformed ECG signals for which the greatest correspondence with the two catheter leads is present.

The above-described comparison is preferably carried out using an error criterion, for example a MSE criterion (mean square error). The comparison furthermore preferably takes place without consideration of differences in the respective signal amplitudes of the ECG reference signals R1, R2 and the transformed ECG signals E1', E2'. In this way, an amplitude error is prevented from being incorporated in the selection of the greatest signal correspondence/least signal deviation and thus corrupting the determination of the first and second transformation angle α1, α2.

Step e) comprises the actual position determination of the catheter tip 3. The position of the catheter tip 3 is determined indirectly via a position determination of the catheter electrode 4. The determination of the position takes place as a function of the previously determined first and second transformation angles α1, α2 and as a function of a position P1 of the first reference electrode 5 and a position P2 of the second reference electrode 7 (FIG. 3). The position PK of the catheter electrode 4 and thus of the catheter tip 3 can be determined by a calculation of an intersection point of two straight lines G1, G2. The straight line G1 extends through the position P1 of the first reference electrode 5 and is inclined by the first transformation angle $\alpha1$ relative to the first coordinate axis X. The second straight line G2 extends through the position P2 of the second reference electrode 7 and is inclined by the second transformation angle $\alpha2$ relative to the second coordinate axis Y. If the transformation angles $\alpha1$, $\alpha2$ and the positions P1, P2 are known, the determination of the intersection point or the position PK is carried out on the basis of fundamentally known geometric determination equations. The evaluation unit 9 is configured for this purpose.

In the embodiment shown, the medical system 1 includes a display unit 15, which is configured to display the determined position PK and is connected to the evaluation unit 9 (FIG. 1). The display unit 15 is shown schematically and very simplified on the basis of FIG. 1 and can include, for example, a display screen, a display, and/or a projection unit for visual display of the position PK. In the embodiment shown, it is provided that the position PK is determined continuously over time or quasi-continuously over time during the advance movement of the catheter in the body. In other words, multiple positions of the catheter tip 3 are determined over time, so that a movement path PK(t) can be determined by means of the evaluation unit 9 and displayed by means of the display unit 15.

The position determination with respect to a planar coordinate system having the two coordinate axis X, Y is illustrated on the basis of FIGS. 2 and 3. It is to be understood that the underlying principle is also applicable to a three-dimensional coordinate system. This is shown on the basis of FIG. 4. A three-dimensional coordinate system having the coordinate axes X, Y, and Z is shown therein. The determination of a third transformation angle $\alpha3$ is required for the three-dimensional position determination. In addition, a third reference electrode 16 is necessary, which is arranged in the present case at a position P3 on the body surface O. The three-dimensional position PK of the catheter tip 3 lies in an intersection point of the straight lines G1, G2, G3. The latter can also be designated as the third straight line G3 and extends through the position P3 of the third reference electrode 16. In this case the third straight line G3 is inclined by the third transformation angle $\alpha3$ relative to the third coordinate axis Z. This axis is oriented orthogonally to the two coordinate axes X, Y.

Figure 4:
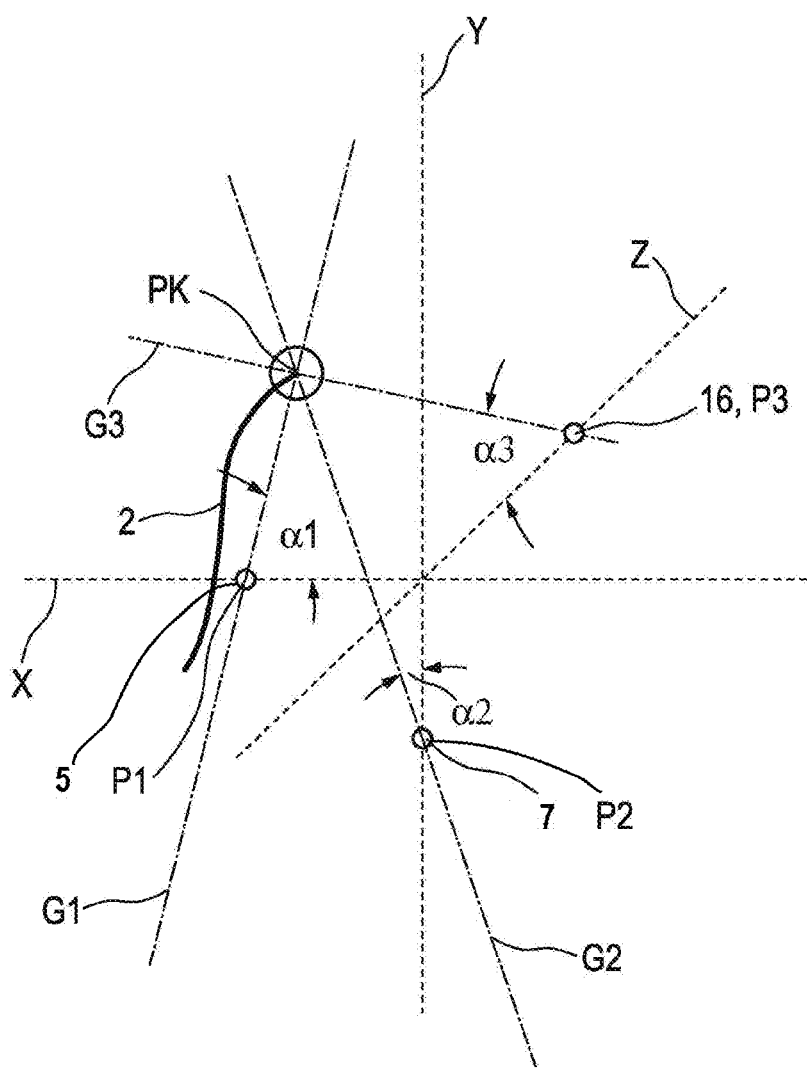
FIG. 4 shows a further view to illustrate the fundamental functionality.

Independently of whether the determination of the position PK takes place in a plane or three-dimensionally, by way of a "over-determination" of the intersection point between the respective straight lines, improved accuracy can be achieved. Accordingly, for example, in the position determination in the plane (FIGS. 2, 3), a further reference electrode is used and a further transformation angle is determined in relation to the first coordinate axis X or the second coordinate axis Y. Visually speaking, with known position of the further reference electrode, a further straight line can be determined and brought into intersection with the straight lines G1, G2. This applies accordingly, mutatis mutandis, with regard to a three-dimensional position determination (FIG. 4).

The invention claimed is:

1. A method for inserting a catheter tip of a catheter into a patient, the method comprising the steps of:
    locating a plurality of electrodes on a body surface of a body of the patient;
    inserting the catheter tip into the body of the patient; and
    advancing the catheter tip in the body of the patient based on determining a movement path of the catheter tip by:
    a) detecting at least one first electrical voltage between a first pair of the plurality of electrodes and detecting at least one second electrical voltage between a second pair of the plurality of electrodes, wherein the first pair of the plurality of electrodes are spaced apart from one another along a first coordinate axis of the body of the patient and the second pair of the plurality of electrodes are spaced apart from one another along a second coordinate axis of the body of the patient, and generating a first ECG signal that represents a first time curve of the at least one first electrical voltage that is assigned to the first coordinate axis, and generating a second ECG signal that represents a second time curve of the at least one second electrical voltage that is assigned to the second coordinate axis;
    b) detecting a first electrical reference voltage between a catheter electrode assigned to the catheter tip and a first reference electrode of the plurality of electrodes on the body surface of the patient, detecting a second electrical reference voltage between the catheter electrode and a second reference electrode of the plurality of electrodes on the body surface of the patient, and generating a first ECG reference signal that represents a time curve of the first electrical reference voltage and generating a second ECG reference signal that represents a time curve of the second electrical reference voltage;
    c) determining a plurality of transformed first ECG signals and transformed second ECG signals for a plurality of different transformation angles using the first ECG signal and the second ECG signal;
    d) determining a first transformation angle of the plurality of different transformation angles, for which a deviation between the corresponding transformed first ECG signal and the first ECG reference signal is minimal, and a second transformation angle of the plurality of different transformation angles, for which a deviation between the corresponding transformed second ECG signal and the second ECG reference signal is minimal; and
    e) determining a position of the catheter tip in relation to a coordinate system formed by the first coordinate axis and the second coordinate axis as a function of the first transformation angle and a position of the first reference electrode and the second transformation angle and a position of the second reference electrode;
    wherein the at least one first electrical voltage, the second electrical voltage, the first electrical reference voltage and the second electrical reference voltage result from electrical activity of cardiac muscle cells of the patient.

2. The method according to claim 1, wherein step c) is carried out using vector ECG data formed at least from the first ECG signal and the second ECG signal.

3. The method according to claim 1, wherein step d) comprises: comparing the signal forms of the different transformed respective ECG signals to the signal form of the respective ECG reference signal, wherein the respective deviation is determined on a basis of an error criterion and/or without consideration of differences in the respective signal amplitudes.

4. The method according to claim 1, wherein at least one further electrical reference voltage is determined between the catheter electrode and a further reference electrode of the plurality of electrodes on the body surface of the patient, and a further ECG reference signal is generated, which represents the time curve of the further electrical reference voltage, and wherein steps d) and e) are carried out in consideration of the further ECG reference signal.

5. The method according to claim 1, wherein the position of the catheter tip is further determined in relation to a three-dimensional coordinate system and as a function of a third transformation angle and a position of a third reference electrode of the plurality of electrodes on the body surface of the patient, which are each assigned to a third coordinate axis.

6. The method according to claim 1, wherein multiple positions of the catheter tip are determined continuously over time during advancing the catheter in the body of the patient, and the movement path of the catheter tip is determined as a function of the determined multiple positions.

7. The method according to claim 6, further comprising displaying the position and/or the movement path of the catheter tip.

8. The method according to claim 1, wherein one electrode of the first pair of the plurality of electrodes is the same as one electrode of the second pair of the plurality of electrodes, such that the first pair of the plurality of electrodes and the second pair of the plurality of electrodes comprise a total of three of the plurality of electrodes.

\* \* \* \* \*